(12) United States Patent
Shimoe et al.

(10) Patent No.: US 6,229,063 B1
(45) Date of Patent: May 8, 2001

(54) DISPOSABLE TRAINING PANTS

(75) Inventors: Nariaki Shimoe; Toshifumi Otsubo; Yasushi Inoue, all of Kagawa-ken (JP)

(73) Assignee: Uni-Charm Corporation (JP)

( * ) Notice: Subject to any disclaimer, the term of this patent is extended or adjusted under 35 U.S.C. 154(b) by 0 days.

(21) Appl. No.: 09/199,533

(22) Filed: Nov. 25, 1998

(30) Foreign Application Priority Data

Nov. 28, 1997 (JP) ..................................................... 9-328220

(51) Int. Cl.$^7$ ....................................................... A61F 13/46
(52) U.S. Cl. ..................... 604/378; 604/381; 604/385.08; 604/385.101
(58) Field of Search .................................. 604/378, 382, 604/381, 385.01, 385.23, 385.101, 385.08

(56) References Cited

U.S. PATENT DOCUMENTS

| | | | | |
|---|---|---|---|---|
| 4,449,979 | * | 5/1984 | Holtman ................................ | 604/379 |
| 5,647,862 | * | 7/1997 | Osborn, III et al. ................. | 604/378 |
| 5,743,776 | * | 4/1998 | Igaue ..................................... | 442/414 |
| 5,846,230 | * | 12/1998 | Osborn, III et al. ................. | 604/378 |
| 5,891,124 | * | 4/1999 | Nomura et al. ...................... | 604/385.1 |
| 5,941,863 | * | 8/1999 | Guidotti et al. ...................... | 604/378 |
| 5,961,505 | * | 10/1999 | Coe et al. ............................. | 604/378 |
| 5,964,743 | * | 10/1999 | Abuto et al. ......................... | 604/385.1 |
| 5,965,468 | * | 10/1999 | Marmon et al. ...................... | 442/340 |
| 6,013,589 | * | 1/2000 | DesMarais et al. .................. | 442/370 |
| 6,015,935 | * | 1/2000 | LaVon et al. ......................... | 604/378 |
| 6,083,210 | * | 7/2000 | Young et al. ......................... | 604/378 |

FOREIGN PATENT DOCUMENTS 7-33916 U    6/1995 (JP) .

* cited by examiner

*Primary Examiner*—Dennis Ruhl
*Assistant Examiner*—Michael Bogart
(74) *Attorney, Agent, or Firm*—Baker & Daniels

(57) ABSTRACT

Training pants having a front region, a rear region and a crotch region therebetween includes a liquid-permeable topsheet, a liquid-impermeable backsheet and an absorbent core disposed therebetween, and the topsheet has a liquid-permeability lower in a transversely middle zone of the crotch region than in transversely opposite side zones, and thereby the pants can give a wearer a feeling of wetness even if the pants have slipped down.

10 Claims, 3 Drawing Sheets

DISPOSABLE TRAINING PANTS

BACKGROUND OF THE INVENTION

This invention relates to training pants for infants.

The training pants of this type are well known, for example, from Japanese Utility Model Application Disclosure Gazette (Kokai) No. Hei7-33916, which includes a wetness sensitive sheet provided on an inner surface of the pants in the middle of its crotch region. The sheet has a high water retaining capacity and adapted to give a wearer discomfortable feeling of wetness upon absorption of urine. The wetness sensitive sheet elastically contracts longitudinally of the crotch region and thereby normally biased to be brought in contact with the wearer's crotch region. Therefore, the wetness sensitive sheet reliably functions to give the wearer a feeling of wetness even if urine is discharged on the pants with its crotch region being not in close contact with the wearer's crotch region.

In the above-mentioned training pants, the wetness sensitive sheet will not be brought in contact with the wearer's crotch region even when the wetness sensitive sheet contracts, so long as the pants have slipped down and the wetness sensitive sheet has been spaced from the wearer's crotch region beyond a limited distance.

SUMMARY OF THE INVENTION

In view of the above problem, it is an object of the invention to provide training pants so improved to achieve its desired training effect even when the pants have slipped down.

According to the invention, there are provide training pants having a front region, a rear region and a crotch region therebetween, the pants comprising a liquid-permeable topsheet, a liquid-impermeable backsheet and a liquid-absorbent core disposed therebetween, a waist-opening and a pair of leg-openings, the openings being respectively provided with elastic members adapted to be stretchable/contractile circumferentially of the respective openings, wherein: of the front and rear waist regions and the crotch region, at least the crotch region is partially composed so that the topsheet has a liquid-permeability which is lower in a transversely middle zone than in transversely opposite side zones of the crotch region.

According to another aspect of the invention, the transversely middle zone of the crotch region has a width in a range of 20~70 mm and the liquid-permeability of the topsheet depends on a total aperture area ratio of plural liquid-permeable apertures formed in the topsheet occupying a total area of the topsheet wherein the total aperture area ratio is in a range of 0~20% in the middle zone and in a range of 5~50% in the transversely opposite side zones, i.e., the total aperture area ratio is higher in the transversely opposite side zones than in the transversely middle zone by 5%.

According to still another aspect of the invention, the transversely middle zone of the crotch region has a width in a range of 20~70 mm and the transversely middle zone of the topsheet is made of a liquid-impermeable nonwoven fabric or a liquid-impermeable plastic sheet while the transversely opposite the zones of the topsheet are made of a liquid-permeable nonwoven fabric or a liquid-permeable apertured plastic sheet.

According to further another aspect of the invention, the total aperture area ratio gradually varies between the transversely middle zone and the transversely opposite side zones.

DESCRIPTION OF THE PREFERRED EMBODIMENT

Specific modes in which the invention may be exploited will be described in detail in reference with the accompanying drawings.

Figure 1:
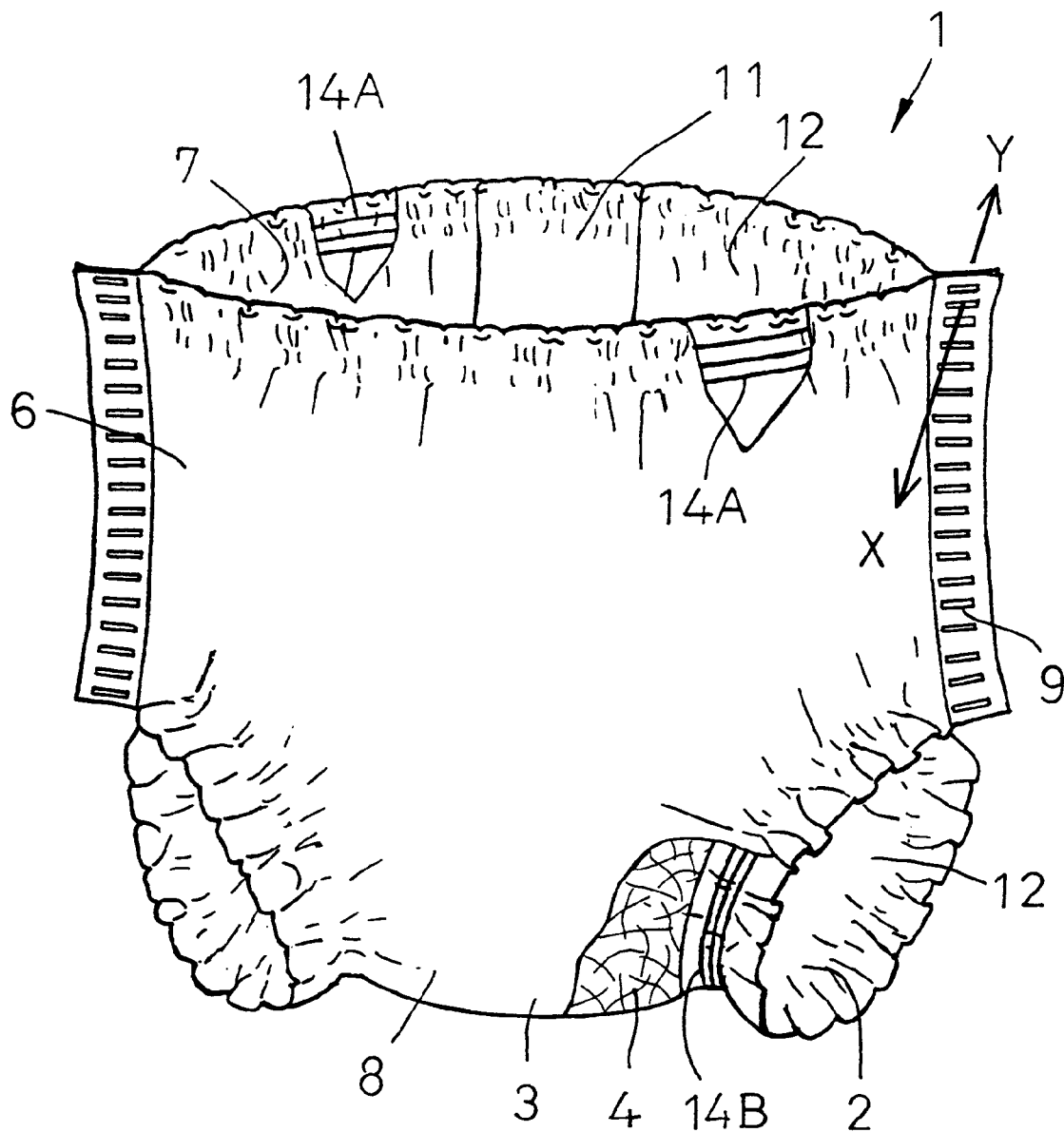
FIG. 1 is a perspective view showing training pants according to the invention as partially broken away.

Training pants 1 shown by FIG. 1 in a perspective view as partially broken away comprises a liquid-permeable topsheet 2, a liquid-impermeable backsheet 3 and an hourglass-shaped liquid-absorbent core 4 disposed between the two sheets 2, 3 so as to define longitudinally a front waist region 6, a rear waist region 7 and a crotch region 8 extending between the front and rear waist regions 6, 7. The front and rear waist regions 6, 7 are placed upon each other along transversely opposite side edges and joined together at vertically arranged intermittent spots 9 along the respective side edges so as to define a waist-opening 11 and a pair of leg-openings 12. The waist-opening 11 is provided along their peripheral edge with a plurality of elastic members 14A and each of the leg-openings 12 is also provided along their peripheral edges with a plurality of elastic members 14B. These elastic members 14A, 14B circumferentially extend between the topsheet 2 and the backsheet 3 and are secured under appropriate tensions to an inner surface of at least one of the topsheet 2 and the backsheet 3.

Figure 2:
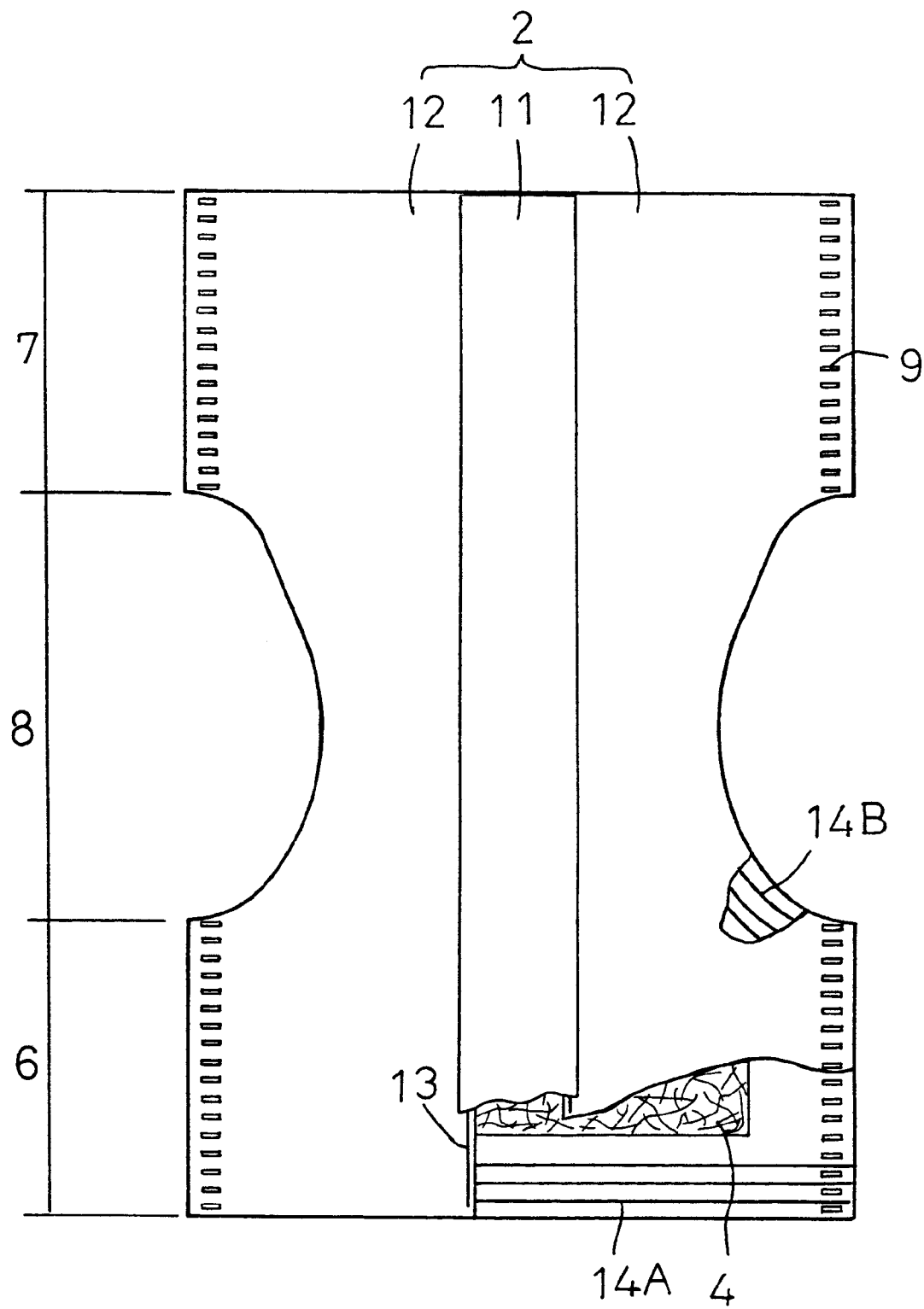
FIG. 2 is a plan view showing the training pants with front and rear waist regions being separated from each other along transversely opposite side edges and longitudinally unfolded, as partially broken away.

FIG. 2 is a plan view showing the training pants 1 with the front and rear waist regions 6, 7 being separated from each other at the joined spots 9 unfolded in a direction X as well as in a direction Y. as partially broken away. As shown, the topsheet 2 comprises a middle sheet 11 occupying a transversely middle zone of the pants 1 and longitudinally extending between respective ends of the front and rear waist regions 6, 7 inclusively of the crotch region 8, and a pair of lateral sheets 12 adjacent respective side edges of the middle sheet 11 and extending therefrom to the respective outermost side edges of the front and rear waist regions 6, 7 and the crotch region 8. The middle sheet 11 and the respective side lateral sheets 12 overlap one another along their adjacent side edges and joined one to another by longitudinal lines 13 of hot melt adhesive.

The middle sheet 11 of the topsheet 2 covers the core 4 over a range of 20~70 mm as measured transversely of the pants 1. The remainder of the core 4 is covered with the lateral sheets 12. The middle sheet 11 may be liquid-impermeable or liquid-permeable and, in the latter case, the middle sheet 11 may have a plurality of first apertures each having a diameter of 0.1~3 mm wetness sensitive means 2 at the maximum total aperture ratio of 20%. The lateral sheets 12 are liquid-permeable and may have a plurality of second apertures each having a diameter of 0.3~5 mm at a total aperture area ratio of 5~50% with respect to the lateral sheets 12. The lateral sheets 12 should have a total aperture area ratio higher than that of the middle sheet 11 so that these lateral sheets 12 may have a liquid-permeability higher than the middle sheet 11.

With the training pants of the arrangement as described above, an amount of urine discharged thereon is scarcely absorbed in the transversely middle zone of the pants 1 but most of such discharged urine flows on the topsheet 1 towards the transversely opposite side edges of the crotch region 8 and then is absorbed by the core 4 through the lateral sheets 12. With the pants 1 of the invention, accordingly, most of discharged urine is collected in the side edges of the crotch region 8, which are normally maintained in close contact with the wearer's legs under the effect of the elastic members 14B and gives the wearer a distinct feeling of wetness. Adjacent these side edges, the core 4 also is indirectly in contact with the wearer's skin through the lateral sheets 12 and the core 4 having absorbed the amount of discharged urine reliably gives the wearer the distinct feeling of wetness for a long period.

The training pants according to the invention gives the wearer the feeling of wetness in such a manner and therefore can achieve the desired training effect even when the pants have slipped down to be clearly spaced from the wearer's crotch region.

Figure 3:
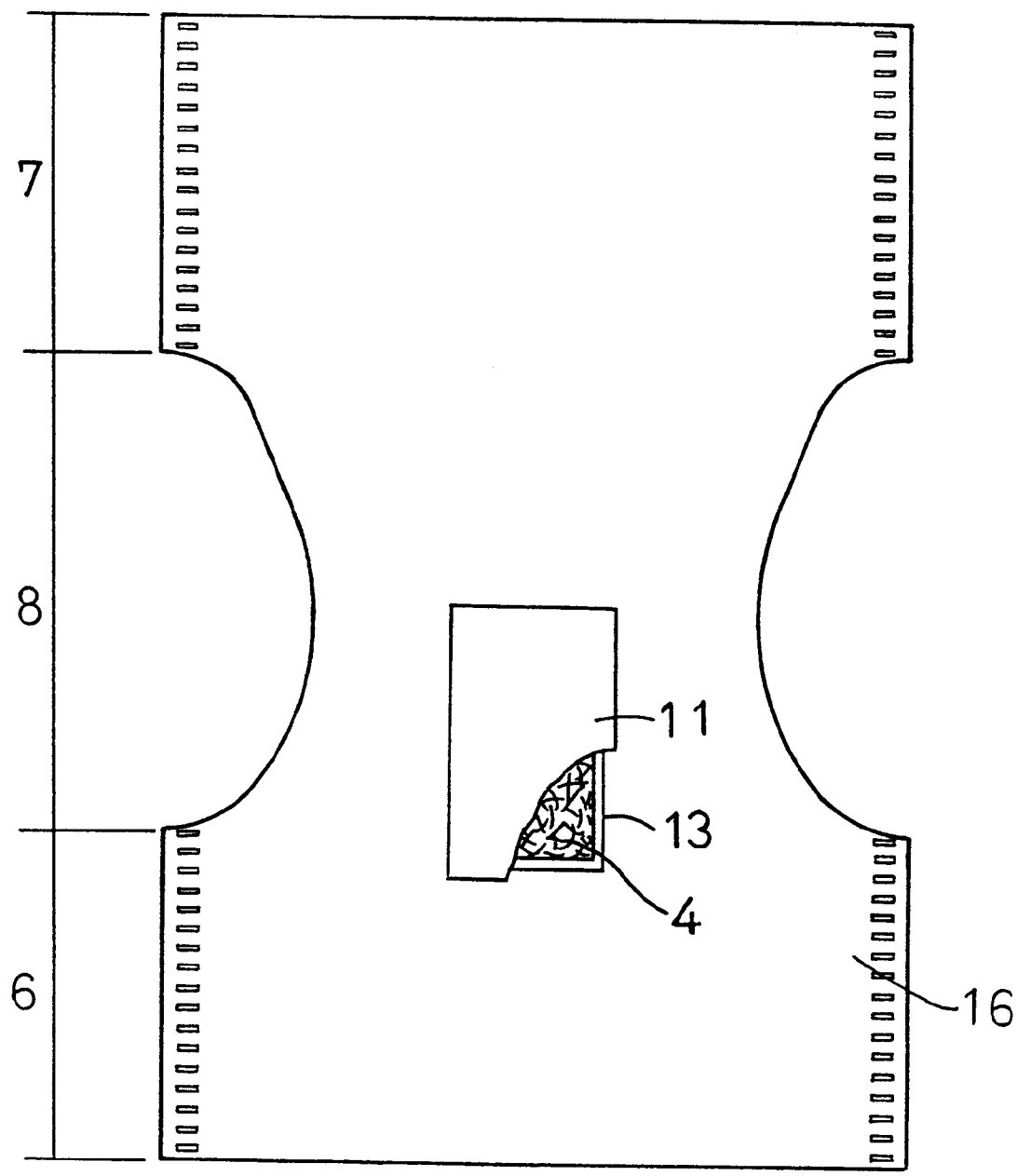
FIG. 3 is a view similar to FIG. 2 showing another embodiment.

FIG. 3 is a view similar to FIG. 2, showing an alternative embodiment of the invention. In training pants 1 shown, the middle sheet 11 is of a relatively small size and provided at a transversely middle location of the crotch region 8 rather adjacent the front waist region 6 at which most of urine will be discharged onto the training pants 1. An inner surface of the pants 1 not covered with the middle sheet 11 is covered with the topsheet 16. Liquid-permeability of the middle sheet 11 is similar to that in the case shown in FIG. 2. The sheet 11 has a width of 20~70 mm and a length of at least 40 mm as measured longitudinally of the pants 1. Liquid-permeability of the topsheet is similar to that of the side sheets 12 in the case shown in FIG. 2. It should be understood that such liquid-permeability of the sheet 16 may be adjusted so as to be progressively enhanced from the middle to the transversely opposite sides.

According to the invention, the middle sheet 11 may be formed by a liquid-impermeable plastic sheet, a liquid-permeable apertured plastic sheet, or a liquid-impermeable or permeable nonwoven fabric. Liquid-permeability of a nonwoven fabric, if it is employed, may be controlled not only by selecting size of each aperture or total aperture area ratio but also by adjusting a basis weight and density of a nonwoven fabric to be used. The side sheets 12 as well as the topsheet 16 also may be formed by a liquid-permeable apertured plastic sheet or a liquid-permeable nonwoven fabric. Liquid-permeability of such nonwoven fabric also may be controlled by adjusting the aperture size, total aperture area ratio, a basis weight and density of the nonwoven fabric. Liquid-permeability of the middle sheet 11, the side sheets 12 and the topsheet 16 may be controlled also by pretreating these sheets so as to make them hydrophilic or hydrophobic.

It is also possible without departing the scope of the invention to cover the entire inner surface of the pants 1 with a single liquid-permeable sheet and then to place the middle sheet 11 upon the single liquid-permeable sheet in the transversely middle zone of the single sheet. However, such arrangement will inevitably lead to wasteful consumption of the sheet material.

It is also possible within the scope of the invention to cover the entire inner surface of the pants 1 with a single sheet which has a liquid-permeability progressively enhanced from the middle zone to the transversely opposite sides of the pants 1.

The training pants according to the invention is characterized by an arrangement such that the transversely opposite side zones may be maintained in close contact with the wearer's skin and most of discharged urine may be collected in these zones before absorbed into the core. Accordingly, the pants can give the wearer a feeling of wetness even if the pants have slipped down and thereby achieve its desired effect. Flow of urine from the middle zone toward the transversely opposite side zones of the crotch region can already given the wearer a discomfortable feeling and the desired effect of the training pants can be additionally achieved in this manner.

What is claimed is:

1. Training pants comprising:
 a front region;
 a rear region; and
 a crotch region positioned between the front region and the rear region,
 said training pants further comprising:
 a liquid-permeable topsheet;
 a liquid-impermeable backsheet;
 a liquid-absorbent core disposed between the liquid-permeable topsheet and the liquid-impermeable backsheet;
 a waist-opening; and
 a pair of leg-openings,
 each of said waist and leg openings being circumferentially provided with stretchable/contractible elastic members,
 said topsheet in at least said crotch region has a transversely middle zone sheet and transversely opposite side zone sheets, and said transversely middle zone sheet having a liquid-permeability which is lower than a liquid-permeability of said transversely opposed side sheets.

2. Training pants according to claim 1, wherein said transversely middle sheet of said crotch region has a width in a range of about 20 to about 70 mm and said liquid-permeability of the topsheet is a function of a total aperture area ratio of plural liquid-permeable apertures formed in said topsheet occupying a total area of said topsheet wherein said total aperture area ratio is in a range of about 0 to about 20% in said transversely middle sheet and in a range of about 5 to about 50% in said transversely opposite side sheets.

3. Training pants according to claim 1, wherein said transversely middle sheet of said crotch region has a width in a range of about 20 to about 70 mm and said transversely middle sheet of said topsheet is made of a liquid-impermeable nonwoven fabric and said transversely opposite side sheets of said topsheet are made of a liquid-permeable nonwoven fabric.

4. Training pants according to claim 2, wherein said total aperture area ratio gradually varies between said transversely middle sheet and said transversely opposite side zones.

5. Training pants according to claim 1 wherein said topsheet in said front and rear waist regions has a liquid-permeability which is lower in a transversely middle sheet than in transversely opposed side sheets thereof.

6. Training pants according to claim 1 wherein, said transversely middle sheet of said crotch region has a width in a range of about 20 to about 70 mm and said transversely middle sheet of said topsheet is made of a liquid-impermeable plastic sheet and said transversely opposite side sheets of said topsheet are made of a liquid-permeable apertured plastic sheet.

7. Training pants according to claim 1, wherein said transversely middle sheet of said crotch region has a width in a range of about 20 to about 70 mm and said liquid-permeability of the topsheet is a function of a total aperture area ratio of plural liquid-permeable apertures formed in said topsheet occupying a total area of said topsheet wherein said total aperture area ratio is higher in said transversely opposite side sheets than in said transversely middle sheet by about 5%.

8. Training pants according to claim 7, wherein said total aperture area ratio gradually varies between said transversely middle sheet and said transversely opposite side sheets.

9. Training pants according to claim 1, wherein said transversely middle sheet of said crotch region has a width in a range of about 20 to about 70 mm and said transversely middle sheet of said topsheet is made of a liquid-impermeable nonwoven fabric and said transversely opposite side sheets of said topsheet are made of a liquid-permeable apertured plastic sheet.

10. Training pants according to claim 1, wherein said transversely middle sheet of said crotch region has a width in a range on about 20 to about 70 mm and said transversely middle sheet of said topsheet is made of a liquid-impermeable plastic sheet and said transversely opposite side sheets of said topsheet are made of a liquid-permeable nonwoven fabric.

* * * * *

UNITED STATES PATENT AND TRADEMARK OFFICE
CERTIFICATE OF CORRECTION

PATENT NO.    : 6,229,063 B1
DATED         : May 8, 2001
INVENTOR(S)   : Shimoe et al.

It is certified that error appears in the above-identified patent and that said Letters Patent is hereby corrected as shown below:

<u>Column 4, claim 4,</u>
Line 54, change "zones" to -- sheets --

Signed and Sealed this

First Day of January, 2002

Attest:

JAMES E. ROGAN
*Attesting Officer*    *Director of the United States Patent and Trademark Office*